United States Patent [19]
Sato et al.

[11] Patent Number: 5,308,867
[45] Date of Patent: May 3, 1994

[54] PLATELET ACTIVATING FACTOR ANTAGONISTS, NAMED "THE PHOMACTINS", THEIR PREPARATION AND USE

[75] Inventors: Aiya Sato; Michihiro Sugano; Kouhei Furuya; Takeshi Oshima; Harumitsu Kuwano; Tadashi Hata; Hideyuki Haruyama, all of Hiromachi, Japan

[73] Assignee: Sankyo Company, Limited, Tokyo, Japan

[21] Appl. No.: 927,847

[22] Filed: Aug. 10, 1992

Related U.S. Application Data

[60] Division of Ser. No. 596,580, Oct. 10, 1990, Pat. No. 5,151,529, which is a continuation-in-part of Ser. No. 440,235, Nov. 22, 1989, abandoned.

[30] Foreign Application Priority Data

Nov. 28, 1988 [JP] Japan .................. 63-300278

[51] Int. Cl.⁵ .................. A01N 43/20; A01K 31/335; C07D 303/00
[52] U.S. Cl. .................. 514/475; 549/545
[58] Field of Search .................. 549/545; 514/475

[56] References Cited

U.S. PATENT DOCUMENTS 3,984,177  10/1976  Trozzolo .................. 549/545
4,076,642  2/1978  Herber et al. .................. 549/545

FOREIGN PATENT DOCUMENTS 136272  10/1980  Japan .

OTHER PUBLICATIONS

P. Braquet et al, "PAF-acether specific binding sites: 2.Design of specific antagonists", Oct. 1986, *Trends in Pharm. Sci.*, vol. 7, pp. 397–403.

Okamoto, et al, "Studies of Platelet Activating Factor (PAF) Antagonists from Microbial Products. I. Bisdethiobis(methylthio)gliotoxin and Its Derivatives", 1986, *Chem. Pharm. Bull.*, 34 340–344.

S. Takase, "Structure of FR900452, a Novel Platelet-Activating Factor Inhibitor from a *Streptomyces*", 1987, *J. Org. Chem.*, 52, 3485–3487.

P. Braquet, et al, "Is there a case for PAF antagonists in the treatment of ishchemic states?", 1989, *Trends in Pharm. Sci.*, vol. 10, pp. 23–30.

*Primary Examiner*—Marianne M. Cintins
*Assistant Examiner*—Rebecca Cook
*Attorney, Agent, or Firm*—Frishauf, Holtz, Goodman & Woodward

[57] ABSTRACT

A series of new compounds, called "the phomactins" is provided and may be isolated from the culture broth of fungi of the genus Phoma. especially Phomas sp. SANK 11486 (No. FERM BP-2598). These compounds are platelet activating factor antagonists and may be used for the treatment of disorders for which known such agents may also be used.

3 Claims, No Drawings

PLATELET ACTIVATING FACTOR ANTAGONISTS, NAMED "THE PHOMACTINS", THEIR PREPARATION AND USE

This application is a division of application Ser. No. 07/596,580 filed Oct. 10, 1990 now U.S. Pat. No. 5,151,529, issued Sep. 29, 1992, which is a continuation-in-part of application Ser. No. 07/440,235 filed Nov. 22, 1989, now abandoned.

BACKGROUND TO THE INVENTION

This application is a division of application Ser. No. 07/596,580 filed Oct. 10, 1990, now U.S. Pat. No. 5,151,529, issued Sep. 29, 1992, which is a continuation-in-part of application Ser. No. 07/440,235 filed Nov. 22, 1989, now abandoned.

The present invention relates to a series of new compounds, to which we have assigned the class name "Phomactin". These compounds may be produced by cultivation of an appropriate microorganism (fungus) of the genus Phoma. The invention also provides a fermentation process for producing these compounds using a novel strain of microorganism of the genus Phoma, as well as the new strain itself, and provides methods and compositions using the new compounds of the invention as platelet activating factor antagonists.

"Platelet activating factor" is herein abbreviated, as is conventional, to "PAF".

Natural PAF, at least as isolated from mammalian tissues, is a mixture of from 2 to 5 phospholipids, the number depending upon the nature of the original tissue. The major constituents of PAF may be represented by the formula (A):

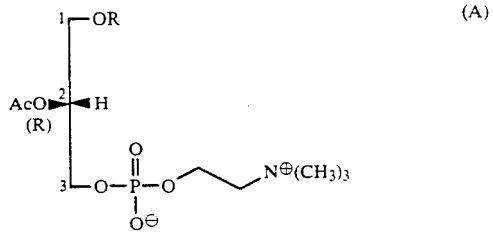

in which R represents a log chain aliphatic hydrocarbon group, which may be saturated or unsaturated. Natural PAF is levorotatory and the various components of natural PAF may be identified, for example as: l-$C_{16:0}$=formula (A) where R represents a hexadecyl group: l-$C_{18:0}$=formula (A) where R represents an octadecyl group: or l-$C_{18:1}$=formula (A) where R represents a 9(Z-octadecenyl group. The convention used above for identifying the constituents of PAF gives the rotation first (l, in the above examples), followed by the number of carbon atoms, and finally the number of double bonds.

PAF exhibits a strong platelet activating and aggregating effect, from which it derives its name. It has, however, in recent years been seen to be a potentially crucial mediator in a wide variety of pathological processs. Thus, it also has a hypotensive effect and increases vasopermeability; it is believed to be an active agent in the induction of the shock state (for example endotoxin-induced shock) and to act as a mediator of inflammatory disease. It has also been found to play a role in cardiac and systemic anaphylaxis, gastric and intestinal ulceration, psoriasis and immune and renal disorders.

It is not, therefore, surprising that, as a result, PAF antagonists have been investigated with a view to developing new types of treatment for the above pathologies, and notably new types of anti-shock agent and anti-inflammatory agent. Accordingly, various compounds have been investigated in an attempt to find such PAG antagonists, and, currently, several compounds are known as PAF antagonists. Although the chemical structure of known PAF antagonists varies widely, and there appears to be no obvious common factor linking their chemical structures, in general, known materials having PAF-antagonist activity may be classified according to their chemical structure as either PAF type or non-PAG type compounds. Of the known compounds. PAF type antagonists are mostly prepared by chemical synthesis, whilst non-PAF type antagonists are mostly recovered from the secondary metabolites of plants and microorganisms. Examples of compounds of the non-PAF type include, for example, ginkgolide (isolated from *Ginkgo biloba*), kadzurenone (isolated from *Piper futokadzura*), veraguensin (isolated from *Magnolia acuminata*), galbengin and galbrabin (isolated from *Himantandra velgravena*), nectandrin A and B (isolated from *Nectandra rigida*), burseran (isolated from *Bursera microphlla*) [details of the above compounds are given by P. Braquet and J. J. Godfroid: Trends in Pharm. Sci., Vol. 7, pp. 397 et seq (1986)], a gliotoxin derivative [isolated from *Penicillium terlikowskii*: M. Okamoto, Chem. Pharm. Bull., 34, 340 (1986)] and a diketopiperazine derivative [isolated from *Streptomyces sp.*: S. Takase, J. Org. Chem., 52, 3485 (1987)].

A variety of PAF-type compounds are known, but these are not relevant to the present invention.

A review of the nature and uses of PAF antagonists is given by P. Braquet et al., Trends in Pharm. Sci., Vol. 10, pp. 23 et seq (1989). Braquet et al examined the effect of BN-52021 (5 mg kg$^{-1}$, given 15 min before coronary artery occlusion) on arrhythmias in mongrel dogs. As shown in Table I, BN-52021 significantly reduced the number of ectopic beats during the 30 min ischemic period. In addition, preliminary studies in rats subjected to coronary artery ligation have shown that BN-52021 (5 mg kg$^{-1}$, i.v. immediately before occlusion), significantly reduced the infarct size as assessed by histological examination after 24 h of occlusion. In the control group the infarct size was 26±2.2% of heart tissue, whereas in the BN-52021-treated group this value was reduced to 17±1.8% (p<0.05).

BN-52021:

| $R_1$ | $R_2$ | $R_3$ |
|---|---|---|
|  |  |  |
| OH | OH | H |

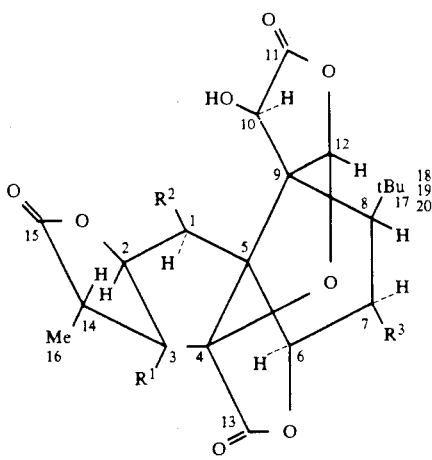

TABLE I

Effect of BN-52021 on arrhythmias evoked by ligation of left anterior descending coronary artery in dogs anesthetized with halothane

| Treatment | n | Number of ectopic beats during 30 min of ischemia, mean ± SEM | | | | |
|---|---|---|---|---|---|---|
| | | 5-10 | 10-15 | 15-20 | 20-25 | 25-30 min |
| Control | 18 | 106 ± 26.0 | 119 ± 33.4 | 208 ± 41.8 | 355 ± 69.5 | 473 ± 104.8 |
| BN-52021 | 7 | 10 ± 5.4* | 10 ± 5.3* | 15 ± 6.3* | 55 ± 28.6* | 98 ± 39.0* |

These cumulative data represent the sum of single ventricular extrasystoles in salvos, and ventricular tachycardia. BN-52021 was introduced in an i.v. bolus of 5 mgkg$^{-1}$ 15 min before coronary artery ligation.
*p < 0.05 (Wilcoxon test).

We have now discovered a series of new PAF-antagonist compounds of the non-PAF type, which we have in accordance with current convention, named "the phomactins", and which can be produced by the cultivation of a microorganism, which we have identified as SANK 11486, which belongs to the species *Phoma* and which has been isolated from the shells of certain crabs.

BRIEF SUMMARY OF INVENTION

In accordance with the present invention, there are provided, as new compositions of matter, novel compounds which we have called the phomactins.

The phomactins are here defined as those compounds having PAF antagonist activity and capable of production by the fermentation of Phoma sp. SANK 11486. In general, the chemical structure of the phomactins is believed to be characterised by a cyclohexene ring which is bridged between a carbon atom of the double bond and a carbon atom 2 positions removed therefrom by a 9 membered carbon bridge structure, which itself may also be bridged.

The invention also provides a process for producing a phomactin by the cultivation of a phomactin-producing microorganism of the strain Phoma, and separating at least one phomactin from the cultured broth.

The invention also provides a pharmaceutical composition for the treatment of inflammation or shock, comprising a PAF antagonist in combination with a pharmaceutically acceptable carrier or diluent, wherein the PAF antagonist is at least one phomactin, as defined above.

The invention will further provides a method of treating a PAF-mediated pathology in a mammal susceptible to such pathology by administering to said mammal an effective amount of a PAF antagonist selected from the group consisting of the phomactins, especially phomactins A and B.

The invention still further provides a method for the treatment or prophylaxis of asthma, inflammation or shock comprising administering an amount of a PAF antagonist to an animal (which may be a mammal, e.g. human) sufficient to effect treatment or prophylaxis of inflammation or shock, wherein said PAF antagonist is at least one phomactin, as defined above.

DETAILED DESCRIPTION OF INVENTION

One of the compounds of the present invention, which we have called "Phomactin A", has the following chemical formula and properties:

1) Chemical formula as shown in formula (I):

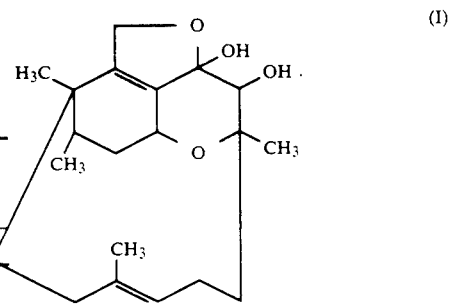

2) Appearance: Colorless oily substance.
3) Specific rotation: $[\alpha]_D^{25} = +146.7°$ (c 0.75, chloroform).
4) Elemental analysis:

| Found: | C, 71.65%; H, 9.10%. |
|---|---|
| Calculated: | C, 71.82%; H, 9.04%. |

5) Molecular formula: $C_{20}H_{30}O_4$ (Determined by high resolution mass spectroscopy).
6) Molecular weight: 334 (Determined by mass spectroscopy).
7) Infrared absorption spectrum, $\nu_{max}$ cm$^{-1}$ (liquid film): 3395, 1580, 1450, 1380, 1230, 1050, 960 and 756.

The infrared absorption spectrum measured as a liquid film is shown in FIG. 1 of the accompanying drawings.

8) $^1$H-Nuclear magnetic resonance spectrum, δ ppm:

The nuclear magnetic resonance spectrum (500 MHz) measured in perdeuterated methanol using tetramethylsilane as an internal standard is shown in FIG. 2 of the accompanying drawings.

9) $^{13}$C-Nuclear magnetic resonance spectrum, δ ppm:

The nuclear magnetic resonance spectrum (126 MHz) measured in perdeuterated methanol using tetramethylsilane as an internal standard is shown in FIG. 3 of the accompanying drawings, and the chemical shifts and multiplicities are shown below:

14.9 (q), 16.5 (q), 19.6 (q), 21.9 (q), 25.8 (t), 27.8 (d), 34.2 (t), 34.5 (t), 37.6 (t), 38.0 (s), 38.6 (t), 62.6 (d), 72.0 (t), 74.6 (d), 81.2 (s), 110.0 (s), 128.7 (s), 131.3 (s), 131.4 (d), 144.6 (s).

(q is quartet, t is triplet, d is doublet and s is singlet).

10) Ultraviolet absorption spectrum, $\lambda_{max}$ nm:

The ultraviolet absorption spectrum measured in ethanol shows end absorption only.

11) Solubility:

Soluble in methanol, ethanol, acetone, ethyl acetate, chloroform, dimethyl sulfoxide, benzene and diethyl ether; and insoluble in water.

12) Color reactions:

Color tests with sulfuric acid and iodine are positive.

13) Thin layer chromatography:

Rf: 0.54.

Adsorbent: Silica gel plate (Kieselgel 60F$_{254}$, Merck).

Developing solvent: a 1:2 by volume mixture of hexane and ethyl acetate.

The systematic name of phomactin A is 3,3a-dihydroxy-2,6-(3'-methyl-3'-hexeno)-2,6,7-trimethyl-3a,5,6,7,8,8a-hexanhydrofuro[2,3,4-de]chroman.

Another of the compounds of the present invention, which we have called "Phomactin B", has the following chemical formula and properties:

1) Chemical formula as shown in formula (II):

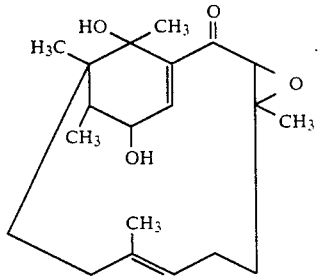

(II)

14) Appearance: Colorless needles, melting at 180°-182° C.

3) Specific rotation: $[\alpha]_D^{25} = +175°$ (c 0.70, chloroform).

4) Elemental analysis:

| | |
|---|---|
| Found: | C, 71.71%; H, 9.09%. |
| Calculated | C, 71.82%; H, 9.04%. |

5) Molecular formula: $C_{20}H_{30}O_4$ (Determined by high resolution mass spectroscopy).

6) Molecular weight: 334 (Determined by mass spectroscopy).

Infrared absorption spectrum, $\nu_{max}$ cm$^{-1}$ (KBr): 3420, 3380, 1669, 1630, 1460, 1392, 1250, 1200, 1080, 1000, 903 and 812.

The infrared absorption spectrum measured on a KBr disk is shown in FIG. 4 of the accompanying drawings.

$^1$H-Nuclear magnetic resonance spectrum, δ ppm:

The nuclear magnetic resonance spectrum (500 MHz) measured in perdeuterated methanol using tetramethylsilane as an internal standard is shown in FIG. 5 of the accompanying drawings.

$^{13}$C-Nuclear magnetic resonance spectrum, δ ppm:

The nuclear magnetic resonance spectrum (126 MHz) measured in perdeuterated methanol using tetramethylsilane as an internal standard is shown in FIG. 6 of the accompanying drawings, and the chemical shifts and multiplicities are shown below:

14.5 (q), 16.4 (q), 19.7 (2×q), 22.7 (t), 23.2 (q), 33.6 (t), 36.7 (t), 37.4 (t), 41.5 (s), 46.3 (d), 62.8 (s), 65.9 (d), 71.4 (d), 73.3 (s), 120.3 (d), 135.6 (d), 136.8 (s), 147.2 (s), 200.1 (s)

(abbreviations as above).

10) Ultraviolet absorption spectrum, $\lambda_{max}$ nm:

The ultraviolet absorption spectrum measured in ethanol shows an absorption at 240 nm (E=2,500).

11) Solubility:

Soluble in methanol, ethanol, acetone, ethyl acetate, chloroform, dimethyl sulfoxide, benzene and diethyl ether; and insoluble in water.

12) Color reactions:

Color tests with sulfuric acid and iodine are positive.

13) Thin layer chromatography:

Rf: 0.51.

Adsorbent: Silica gel plate (Kieselgel 60F$_{254}$, Merck).

Developing solvent: a 1:2 by volume mixture of hexane and ethyl acetate.

The systematic name of phomactin B is 13,15-dihydroxy-3,4-epoxy-2-oxo-4,8,11,12,15-pentamethyl-bicycl[9.3.1]pentadeca-7,14-diene.

The phomactins of the present invention can exists in the form of various stereoisomers and geometric isomers, although, in the form as naturally produced by a microorganism of the genus Phoma, the compounds of the present invention will normally exist as a single isomer. In the formulae given above, the individual isomers and mixtures of the isomers are represented by a single formula. However, the present invention covers not only the individual isomers but also mixtures of any two or more isomers, whether naturally produced or produced by chemical manipulation. Where the naturally produced isomer is not the one desired, the desired isomer may be produced by chemical means, as is well known in the art.

It is currently believed that the configurations of phomactins A and B are as shown in formulae (Ia) and (IIa), respectively:

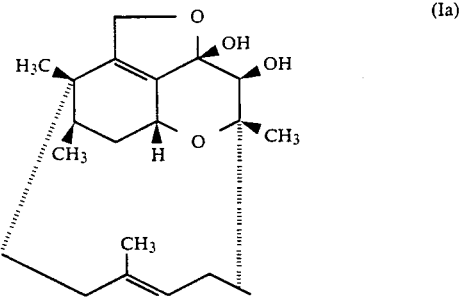

(Ia)

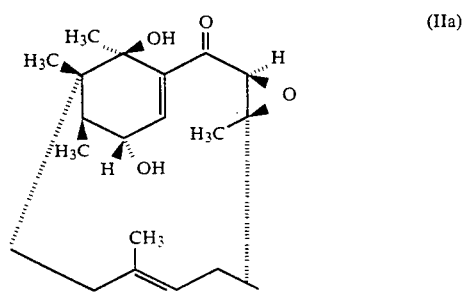

(IIa)

The phomactins have been produced by the cultivation of a strain of microorganism of the genus Phoma (a fungus), which we have designated strain SANK 11486. This phomactin-producing microorganism of the strain SANK 11486 employed in the present invention was isolated by us from the shell of a crab. Chinoecetes opilio (colloquially called "susugani", which is a crab whose shell turns black) collected in the vicinity of the coast at Fukui prefecture, Japan.

The microbiological properties of the strain are as follows:

Growth on oatmeal agar at 25° C. reached a 20 mm diameter in 7 days and 38 mm in 14 days. On both of the these days, the colonies had a wet velvety appearance and a greenish gray color.

On the oatmeal agar, only mycelia were observed, but no spores or conidia; however, on oatmeal agar prepared with an artificial sa water (Brand name: Jamarin S) it forms pycinidia in which conidia are produced.

The pycnidium is observed as a semispherical or pyriform shape of dimensions 80–120×80–150 $\mu$m and it has a hole in the center thereof. The diameter of the hole is 5–15 $\mu$m and there are brown setae of dimension 20–50×2–4 $\mu$m on the periphery.

The conidiophore is not particularly differentiated, and the inner most layer of phore wall became phialide. The condiophore is colorless, single cellular, elliptical or elongated elliptical of dimensions 2.5–4.0×2.0–2.5 $\mu$m.

The strain does not grow at 37° C.

Based upon the above features, and referring to standard texts [B.C. Sutton, "The Coleomycetes", Commonwealth Mycological Institute, 19880; and J. Kohlmeyer and E. Kohlmeyer, "Marine Mycology, The Higher Fungi", Academic Press, 1979] the present strain was identified as a new strain of a known species, Phoma sp., and was given a stock number SANK 11486 (No. FERM P-10364). The color expressions and codes used herein were assigned according to the directions in the Methuen Handbook of Color, 3rd Ed. (1978), written by A. Kornerup and J. H. Wanscher, and published by Eyre Methuen, London.

The strain was deposited by us at the Fermentation Research Institute, Agency of Industrial Science and Technology, Tokyo, Japan with the accession No. FERM P-10364 and was redeposited under the conditions prescribed by the Budapest Treaty on 20 September 1989 under the accession No. FERM BP-2598.

It has been established that strain SANK 11486 produces the phomactins. However, as is well known, the properties of fungi in general can vary considerably and such fungi can readily undergo mutation, both through natural causes and as the result of induction by artificial means. Accordingly, the process of the present invention embraces the use of any microorganism which can be classified within the genus Phoma, especially strains of species of the genus Phoma to which the new strain SANK 11486 belongs, and which shares with strain SANK 11486 the characteristic ability to produce the phomactins. It is a matter of simple experimentation to determine, on the basis of the information given herein regarding the properties of the phomactins, notably the biological properties, whether any given strain produces any of the phomactins or produces it or them in sufficient quantity to render that strain of potential commercial interest.

The novel compounds, the phomactins, of the present invention may be prepared by the cultivation of any of these strains of fungus in culture media of the type conventionally used for the production of other fermentation products from similar microorganisms. Such media necessarily contain microbiologically assimilable salts, as is well known to those skilled in the art. In all respects, however, the culture media employable in the present invention are the same as those known for the cultivation of known strains of fungi.

Preferred examples of carbon sources include: glucose, fructose, maltose, sucrose, mannitol, glycerol, dextrin, oats, rye, corn starch, potato, potato starch, corn meal, soybean meal, cottonseed cake, cottonseed oil, molasses, citric acid, tartaric acid and the like, preferably glucose, sucrose or potato or any combination thereof. Such compounds can be used alone or in any suitable combination. In general the amount used may vary in the range of from 1 to 10% by weight of the culture medium.

Preferred nitrogen sources are normally protein-containing materials, but they may be other materials, including inorganic materials, such as are commonly used in a fermentation process. Examples of such nitrogen sources include: soybean meal, wheat bran, peanut meal, cottonseed cake, cottonseed oil, cottonseed meal, casein hydrolyzates, pharmamin, fish meal, corn steep liquor, peptone, meat extract, yeast, yeast extract, salt extract, sodium nitrate, ammonium nitrate, ammonium sulfate and the like, preferably peptone and/or meat extract. These nitrogen sources may be used alone or in any suitable combination. In general, we prefer to employ them at a concentration between 0.2 and 6% by weight of the culture medium.

The nutritive inorganic salts that should be added to the culture medium are conventional salts that are capable of providing various ions necessary to the growth of microorganisms, such as sodium, ammonium, calcium, phosphate, sulfate, chloride and carbonate ions. In addition, the medium should preferably contain minor amounts of other essential metals, such as potassium, calcium, cobalt, manganese, iron and magnesium.

The aqueous component of the culture medium may, as illustrated in certain of the examples hereafter, be provided by a form of sea water, whether natural or (as is preferred) artificial; however, equally good results are achievable using ordinary water, and the use of a form of seat water is, therefore, unnecessary to the present invention.

When the process of the present invention is carried out by a liquid culture technique, an antifoaming agent, such as a silicone oil, a plant oil or a surface-active agent, is preferably used in the culture medium.

The pH of the culture medium for producing the phomactins by the cultivation of Phoma sp. SANK 11486 preferably varies within the range of from 5.0 to 9.0 and is more preferably from 6.5 to 8.5.

The cultivation may be carried out at any temperature within the range of from 15° to 30° C., although a temperature of from 20° to 28° C. is preferred for good growth, and a temperature of from 22° to 26° C. is preferred in order to optimize the production of the phomactins.

The phomactins are produced under aerobic culture conditions and conventional aerobic culture methods. such as solid culture, shaking culture and aeration-stirring (submerged) culture methods, may be used. In the case of small scale cultivation, shaking culture for a period of from several days to two weeks at a suitable temperature, such as 22°–26° C., is typical. In such a small scale culture method, the culture may be initiated with 1 or 2 proliferation steps, producing seed cultures in, for example, Erlenmeyer flasks, fitted with baffle plates, which serve as a liquid flow regulator. The medium for the seed culture steps preferably contains both carbon and nitrogen sources, as indicated above for the cultivation steps. In the preferred sequence of operations for such small scale cultivation, the seed culture flasks are shaken in a constant temperature incubator at, for example, 22°-26° C. for 7 days or until sufficient growth is achieved. The grown seed culture is then transferred to a second seed medium or to the production medium. When an intermediate growth phase is used, essentially the same method is used for growth, and an aliquot of the resulting intermediate product is inoculated into the production medium. The inoculated flask may be incubated for several days whilst shaking, at a suitable temperature, e.g. 22°-26° C., and, after completion of the incubation, the contents of the flask may be centrifuged or filtered.

In the case of large scale production, the use of an appropriate fermentor equipped with a stirrer and an aeration apparatus is preferred. In this case, the nutritive medium can be prepared inside the fermentor. The medium is preferably first sterilized by elevating the temperature to sufficiently high temperature, such as 125° C.; after cooling, the sterilized medium may be inoculated with the previously prepared seed culture. The culture then proceeds under stirring and aeration at a suitable temperature, e.g. 22°-26° C. This method is suitable for obtaining the compound of the present invention in a large amount.

The progress of the cultivation and the amount of the phomactins produced as the culture proceeds can be determined by various well known techniques, which are conventionally used in this art. For example, it may be monitored by following the increase in anti-PAF activity of the culture broth. Generally, the total amount of phomactins produced is believed to reach a maximum between 10 and 14 days after initiation of the fermentation, but the exact time will vary depending upon the temperature and other fermentation conditions; however, the exact optimum time for any given set of conditions can easily be determined by monitoring the progress of the production of the phomactins, as suggested above.

After completion of the cultivation, the phomactins present in the liquid fraction of the cultured mass may be separated by filtration, preferably using a filter aid such as diatomaceous earth, or by centrifugation or by any other standard technique. The phomactins present in the filtrate or in the supernatant can be recovered by extraction from this filtrate and/or they may be purified utilizing the physiochemical properties of the phomactins. For example, the phomactins present in the filtrate or the supernatant can be extracted at a neutral pH with one or more water immisible organic solvents (such as diethyl ether, ehtyl acetate, hexane, chloroform, ethylene chloride or methylene chloride), and the solvents may be used individually or as a mixture.

An alternative method is to use an adsorption agent, for example activated charcoal, or an adsorption resin, such as an Amberlite (trade mark) XAD-2 or XAD-4 resin (Rohm and Haas Co., Ltd.), or a Diaion (trade mark) HP-10, HP-20, CHP-20P or HP-50 resin (mitsubishi Kasei Corporation). The fluid containing the phomactins is passed through a layer of one of these adsorbents in order to remove the adsorbed impurities or the adsorbed phomactins are eluted with a suitable eluent, such as aqueous methanol, aqueous acetone or aqueous butanol. Almost all of the phomactins produced is believed to be released into the culture medium, and very little is thought to be retained in the cells; however, if it is desired to recover any phomactins that may be retained in the cells, this may be achieved by conventional means.

The phomactins obtained as described above can be further purified by various conventional techniques, notably the various chromatography techniques, such as adsorption column chromatography using a carrier such as silica gel or a magnesia-silica gel, such as Florisil (trade mark), partition column chromatography using Sephadex (trade mark) LH-20 (Pharmacia Fine Chemicals), or high performance liquid chromatography using a column for a normal or reverse phase process.

At any suitable stage in the above procedure, the several phomactins may be separated from each other by conventional methods, of which the chromatography techniques, notably column chromatography, are the most effective. It is, therefore, convenient to separate the phomactins in the course of the purification procedure outlined above.

The phomactins of the present invention are new compounds which have not previously been described in the literature. They have been shown to exert a PAF antagonist activity in test animals and are therefore expected to demonstrate a similar activity in other animals (e.g. humans, dogs, cats and rabbits). They are thus expected to be useful as an antithrombotic drug. and are also expected to be useful for the prophylaxis and therapy of inflammation, shock, asthma, peptic ulcers, renal failure, hypertension, ischemia and similar disorders which may be relieved by the administration of PAF antagonists.

Although it has not been established with certainty and we do not wish to be limited by any theory, it is currently believed that the phomactins operate as PAF antagonists by binding to PAF receptors in place of PAF itself. This mode of operation appears to be common to several types of PAF antagonists, despite widely differing chemical structures.

One or more of the phomactins of the present invention may be used alone as a therapeutic or prophylactic drug, or it or they may be mixed with pharmaceutically acceptable carriers and/or excipients and/or diluents appropriate to its or their intended route of administration, as is well known in the art. For example, for oral administration, the drug may be employed in the form of powders, granules, tablets or capsules; for parenteral administration, the drug may be employed in the form of injections. The dosage of the compounds of the present invention will vary, depending upon the severity and nature of the disease or disorder, the age, body weight and condition of the patient and upon the route, frequency and period of administration. However, a suitable daily dose of the phomactin or phomactins of the present invention for an adult human by an enteric route would be in the range of from 1 mg to 1,000 mg, which may be administered as a single dose or as divided doses e.g. from one to several times per day.

The preparation of the compounds of the present invention is further illustrated by the following non-limiting Examples.

EXAMPLE 1 a) Cultivation

One loopful of Phoma sp. SANK 11486 from a slant culture was inoculated into a 500 ml Erlenmeyer flask fitted with baffles (seed flask) and containing 100 ml of a seed culture medium having the composition described below.

| Composition of medium | |
|---|---|
| Sucrose | 20 g |
| Potato | 100 g |
| Peptone | 10 g |
| Monobasic potassium phosphate | 5 g |
| Artificial sea water (Brand name: Jamarin S, Jamarin Laboratories Co. Ltd.) pH 8.5 | 1,000 ml |

The whole of the resulting culture broth was then cultivated at 26° C. for 7 days on a 200 rpm rotatory shaker (7 cm radius gyration).

100 ml of a culture medium (having the same composition as that of the seed culture medium) were put into each of 120×500 ml Erlenmeyer flasks, and the medium in each flask was sterilized. 3 ml of the seed culture was then inoculated into each flask. The material in each of the 120 flasks was then subjected to shaking culture under the same conditions as were used for the seed culture for 7 days.

b) Isolation

The whole of the cultured broth from all 120 flasks was combined and filtered with suction, to give 13 liters of a filtrate. This was then extracted twice, each time with an equal volume of ethyl acetate. The ethyl acetate extracts were combined and washed with 5 liters of water; they were then dried over anhydrous sodium sulfate, after which they were evaporated to dryness under reduced pressure using a rotary evaporator, to give 360 mg of oil substance. The whole of this oily substance was purified by adsorption column chromatography through 30 times its own volume of silica gel (Art. 9385, 230-400 Tyler standard mesh, Merck), eluted with a 1:1 by volume mixture of hexane and ethyl acetate. The fractions showing PAF antagonist activity were collected, and the solvent was removed by distillation under reduced pressure to give 130 mg of oily material. The whole of this oily material was further purified by reverse phase column chromatography (Lobar RP-8 column, size B, Merck). The fractions eluted with 80% by volume aqueous methanol were collected and the solvent was distilled off. The resulting residual oily material was purified by high performance liquid chromatography (Senshu pack ODS-2251-S, Senshu Kagaku Co., Ltd.) using 40% by volume aqueous acetonitrile as the eluent. The collected fractions were freed from the solvent by distillation under reduced pressure to afford 3 mg of the desired compound, phomactin A {Chemical name: (3'E)-3,3a-dihydroxy-2,6-(3'-methyl-3'-hexeno)-2,6,7-trimethyl-3a,5,6,6,8,8a-hexahydrofuro[2,3,4-de]-chroman}, as a colorless oil.

EXAMPLE 2

The whole of the culture broth obtained by culturing a seen culture in 480 flasks under the same conditions as described in Example 1 was filtered, with the aid of suction, and the resulting 48 liters of filtrate were twice extracted, each time with an equal volume of ethyl acetate. The combined ethyl acetate extracts were washed with 20 liters of water and dried over anhydrous sodium sulfate, after which they were evaporated to dryness under reduced pressure using a rotary evaporator, to give an oil substance. This oily substance was subjected to silica gel column chromatography through about 30 times its own volume of silica gel (Art. 9385, 230-400 mesh Tyler, Merck), eluted with a 1:1 by volume mixture of hexane and ethyl acetate and then with a 2:3 by volume mixture of hexane and ethyl acetate. The first fraction was concentrated by evaporation under reduced pressure and purified by reverse phase column chromatography (Lobar RP-8 column, size B, Merck) and high performance liquid chromatography (Senshu pack ODS-2251-S, Senshu Kagaku Co., Ltd.) as described in Example 1, to give 9.4 mg of phomactin A as a colorless oil. The second fractions eluted with the 2:3 mixture were concentrated by evaporation under reduced pressure to give 78.2 mg of oil substance, which was further purified by silica gel column chromatography (Lobar Si60 column, size A, Merck) eluted with a 1:1 by volume mixture of hexane and ethyl acetate. The resulting active fractions were then subjected to reverse phase column chromatography (Lobar RP-8 column, size B, Merck) eluted with 60% by volume aqueous methanol to give 15.9 mg of phomactin B {Chemical name: (7E)-13,15-dihydroxy-3,4-epoxy-2-oxo-4,8,11,12,15-pentamethylbicyclo[9,3,1]pentadeca-7,14-diene} as colorless needles.

EXAMPLE 3

A seed culture was cultured in 55 flasks at 23° C. for 11 days in a similar manner to that described in Example 1, except that tap water was used instead of artificial sea water. The whole of the resulting culture broth was filtered, with the aid of suction, and 5.4 liters of the resulting filtrate was extracted twice with the same volume of ethyl acetate. The combined ethyl acetate extracts were washed with water and dried over anhydrous sodium sulfate, after which they were evaporated to dryness under reduced pressure using a rotary evaporator, to give 636 mg of an oily substance. The whole of this oil substance was subjected to silica gel column chromatography (Art. 9385, 230-400 mesh Tyler, Merck) eluted with a 1:4 by volume mixture of hexane and ethyl acetate. The active fractions were concentrated by evaporation under reduced pressure, to give 274 mg of oily substance. This was further purified by high performance liquid chromatography (Senshu pack ODS-2251-S, Senshu Kagaku Co., Ltd.) eluted with 80% by volume aqueous methanol at a flow rate of 6 ml/min to give 14.0 mg of phomactin A with a retention time of 22.5 minutes. The fraction preceding the phomactin A-containing fraction was concentrated by evaporation under reduced pressure, and purified by high performance liquid chromatography (Senshu pack ODS-2251-S, Senshu Kagaku Co., Ltd.) eluted with 70% by volume aqueous methanol at a flow rate of 6 ml/min to give 14.4 mg of phomactin B with a retention time of 18 minutes.

EXPERIMENT 1

The following antiplatelet aggregation test was performed, using the phomactin A thus obtained.

Blood was drawn from a rabbit heart and immediately mixed with nine times its volume of a 3.8% w/v aqueous solution of sodium citrate. A platelet-rich plasma (PRP) was then obtained as a supernatant by centrifugation of the blood mixture at 150×g for 15 minutes at room temperature. The precipitated fraction remaining from the blood mixture was then centrifuged for a further 15 minutes at 10,000×g to obtain a platelet-poor plasma (PPP) as a supernatant. Appropriate proportions of the PRP and the PPP were mixed to obtain a plasma having a platelet count of $6 \times 10^5/\mu l$.

Platelet aggregation was determined by the method of Born et al. [Nature, 194, 927–929 (1962)] where an increase in light transmission through the test sample is measured by means of an aggregometer.

3 μl of a dimethyl sulfoxide solution containing the compound to be tested at an appropriate concentration was added to 250 μl of a saline solution of synthetic $C_{16:0}$ PAF (at a concentration sufficient to give a final concentration of $1 \times 10^{-8} - 3 \times 10^{-8}M$) was added and aggregation was observed for 5 minutes. The aggregation resulting from the addition of the PAF alone, without the prior addition of the test compound, was taken as 100%.

Instead of the test solution, physiological saline was added and the aggregation at one minutes after the addition of $C_{16}$-PAF was used as the control. As a result, phomactin A was found to inhibit platelet aggregation by about 91.7% at a concentration of 10 g/ml, which corresponds to an $IC_{50}$ (i.e. the concentration necessary to inhibit aggregation by 50%) of 17 μM.

The same experiment was carried out with phomactin B. whose $IC_{50}$ was also found to be 17 μM, indicating a good and useful ability to inhibit platelet aggregation.

We claim:

1. The compound of formula (II):

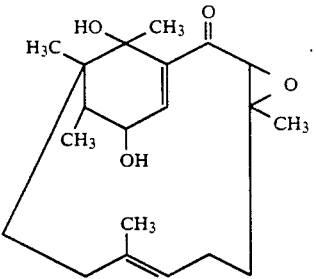

(II)

2. The compound of formula (IIa):

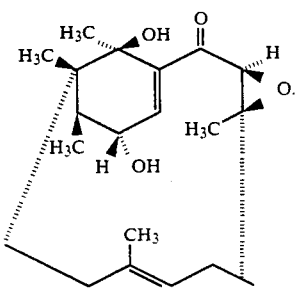

(IIa)

3. A pharmaceutical composition 1 of 2 comprising the compound of claim 2 or 4 in combination with a pharmaceutically acceptable carrier or diluent.

* * * * *